(12) United States Patent
Verbruggen

(10) Patent No.: US 6,815,684 B2
(45) Date of Patent: Nov. 9, 2004

(54) ANALYTICAL X-RAY APPARATUS PROVIDED WITH A SOLID STATE POSITION SENSITIVE X-RAY DETECTOR

(75) Inventor: Raymond Wilhelmus Herman Johannes Verbruggen, Almelo (NL)

(73) Assignee: PANalytical B.V., Almelo (NL)

(*) Notice: Subject to any disclaimer, the term of this patent is extended or adjusted under 35 U.S.C. 154(b) by 82 days.

(21) Appl. No.: 10/008,335

(22) Filed: Nov. 8, 2001

(65) Prior Publication Data

US 2002/0053641 A1 May 9, 2002

(30) Foreign Application Priority Data

Nov. 8, 2000 (EP) .............................. 00203925

(51) Int. Cl.[7] .............................................. G01T 1/24
(52) U.S. Cl. .............................. 250/370.09; 250/370.14
(58) Field of Search ................... 250/370.14, 370.1, 250/370.09

(56) References Cited

U.S. PATENT DOCUMENTS 5,113,077 A  5/1992  Shimizu et al. ........ 250/370.11
6,114,874 A * 9/2000  Bales ........................... 326/66
6,573,762 B1 * 6/2003  Wessendorf et al. ... 250/370.01

* cited by examiner

Primary Examiner—Constantine Hannaher
(74) Attorney, Agent, or Firm—Jensen & Puntigam PS

(57) ABSTRACT

Each detector element 44 in a solid state position sensitive detector (PSD) could provide a low charge efficiency per X-ray quantum; moreover, a comparatively high stray capacitance 104 could exist between the take-off electrode 90 and the semiconductor material 86, 88, 92 whereto it is connected. These effects will give rise to a low signal-to-noise ratio, thus degrading the signal. According to the invention, the analog charge amplifiers 58 are constructed in integrated bipolar technology and their read-out circuitry 48 is embodied in digital technology, preferably in a BICMOS process in the form of the Current Mode Logic (CML) technique. Moreover, the digital signal processing circuitry may be accommodated on the same substrate as the charge amplifiers.

3 Claims, 5 Drawing Sheets

ANALYTICAL X-RAY APPARATUS PROVIDED WITH A SOLID STATE POSITION SENSITIVE X-RAY DETECTOR

The invention relates to a device for analysis of materials by means of radiation, including
- a radiation source for producing the radiation,
- a sample location for accommodating a sample of the material to be analyzed,
- a position sensitive detection device for detecting the radiation emanating from the sample,
which detection device includes
- an array of radiation sensitive detector elements,
- an electronic read-out circuit which is connected to the detector array and includes charge amplifiers in a one-to-one relationship with the detector elements, the input of said charge amplifiers being connected to a respective one of the detector elements.

For the analysis of materials by means of radiation, notably X-rays, it is practically always necessary to measure the angle at which the radiation emanates from the sample relative to the direction of the incident beam. Measurement may concern a large angular range (of the order of magnitude of 180 degrees) or a smaller angular range when general knowledge has already been acquired as regards the angular distribution of the radiation in a given angular range. The latter is the case when, for example, the fine structure of an X-ray diffraction line is to be measured. In that case a position sensitive detection device can be used, that is, a detector which is provided with an array of adjacently situated (generally linear) radiation sensitive detector elements; the position of an element that is activated by radiation is then a measure of the angular direction in which the radiation emanates from the sample. In that case it is not necessary to use a detector that is adjustable in respect of angle; this offers considerable structural advantages.

United States patent U.S. Pat. No. 5,113,077 discloses a device for the detection of radiation in an apparatus for scanning an object by means of X-rays for computed tomography ("X-ray CT scanner"). The CT scanner described in the cited patent is provided with a position sensitive detection device for the detection of the X-rays emanating from an object to be examined. Said detection device includes an array of radiation sensitive detector elements in the form of a scintillator with photodiodes. An electronic read-out circuit is connected to each detector element, which read-out circuit includes charge amplifiers which are connected to the detector elements in a one-to-one relationship in such a manner that the input of a charge amplifier is connected each time to the output of one of the respective detector elements. Each of the charge amplifiers is constructed as a fed-back operational amplifier (OPAMP). A separate PNP transistor is connected to the output of the operational amplifier in such a manner that the output current of the combination formed by the OPAMP and the transistor is formed by the emitter current of the PNP transistor.

Analysis of materials by means of X-rays often utilizes comparatively soft X-rays, for example the $K_\alpha$ radiation of copper that has a wavelength of approximately 0.154 nm. The charge yield of a solid state detection element is comparatively small in the case of such comparatively soft X-rays. For example, per incident X-ray quantum an amount of charge corresponding to 2200 electron-hole pairs will be excited in a silicon detector consisting of a body of N material adjoining on the one side a PN junction and on the other side an $N^+$ layer. In practice it is usually not possible to increase the X-ray yield of such a position sensitive detector by increasing the X-ray sensitive surface, because the dimensions of said surface determine the position resolution and hence are preferably kept as small as possible. Furthermore, the size of the surface of the detector element that is exposed to the X-rays defines the size of the take-off electrode. The combination of this take-off electrode and the semiconductor material on which it is arranged determines the value of the (stray) capacitance at the output of the detector element, that is, at the input of the subsequent charge amplifier. It is a generally known fact in such amplifier technology that the capacitance at the input of such an amplifier determines the noise contribution by said amplifier in the amplifier chain, meaning that the noise contribution will be higher as the input capacitance is higher.

Both of the above-mentioned effects (low charge yield per X-ray quantum and high input capacitance) lead to a comparatively low, that is, poor signal-to-noise ratio in the electronic read-out circuit of the detection device. In principle it is not impossible to enhance the signal-to-noise ratio by way of a longer measuring time; however, such a longer measuring time is undesirable because the comparatively expensive analysis apparatus would then take an undesirably long period of time for carrying out a measurement so that its efficiency would be very low.

In order to mitigate the described problem, it is an object of the invention to provide a device of the kind set forth in which the signal-to-noise ratio can be kept as high as possible during the further signal processing. To this end, the device in accordance with the invention is characterized in that the charge amplifiers (58) are constructed in the integrated bipolar technique, and that the electronic read-out circuit (48) includes signal processing circuits which are connected to the outputs of the charge amplifiers and are constructed in the digital technique.

The invention is based on the recognition of the fact that the stray input capacitance of the charge amplifier makes an important contribution to the noise. In order to minimize the noise contribution at that area, the integrated bipolar technique, causing a comparatively small amount of noise, is used for the charge amplifiers. The further signal processing should then take place at a speed which is high enough so as to avoid unnecessary limiting of the count rate and hence the throughput speed of the samples to be analyzed. This speed can be realized by way of signal processing circuits constructed in the digital technique. Moreover, circuits having a digital construction offer the additional advantage that they can be integrated with a comparatively small circuit surface area and that they can be constructed in such a manner that their power consumption is comparatively low. The requirements as regards small circuit surface area are even more severe since a sufficiently high count rate is required for the detector array; in order to achieve this, each detector element is provided with its own signal processing circuit, thus giving rise to a large number of processing circuits and hence a large surface area occupied by integrated circuits. In order to keep this surface sufficiently small nevertheless, use is made of the digital technique whose requirements as regards space are comparatively moderate.

It is to be noted that from the cited patent U.S. Pat. No. 5,113,077 it is known to provide the charge amplifier with a separate output transistor in the form of a PNP transistor (so a bipolar transistor). However, the cited patent does not provide any information concerning the technology used to construct the charge amplifiers themselves, that is, the circuits that are in direct contact with the stray input capacitance.

The digital signal processing circuits in a preferred embodiment are accommodated on the same substrate as the charge amplifiers. In order to realize a high position resolution and a large measuring range, preferably an as large as possible number of detector elements is used in a position sensitive detector array. This means that a one-to-one relationship between the charge amplifiers and the detector elements necessitates the use of an at least equally large number of connections. If each of the bipolar circuits and the circuits constructed in the digital technique were to have a respective substrate of its own, an equal number of bond pads would have to be provided for each connection on each substrate; as is known, bond pads occupy a large amount of space on the relevant integrated circuit. The above step offers the advantage that said bond pads can be dispensed with.

The digital signal processing circuits in a further embodiment of the invention are constructed by means of a BICMOS process in the form of the Current Mode Logic (CML) technique. If the digital signal processing circuits were constructed in the customary CMOS logic, upon transition from a first logic state to the complementary logic state a pulse-shaped peak current (also referred to as a reactive current) would occur from the transistors of the switched logic gates to the substrate on which they are provided. Because the charge amplifiers that are constructed in the bipolar technique are also mounted on the same substrate, such pulse-shaped leakage currents are liable to contribute to the noise of the charge amplifiers, thus degrading the signal-to-noise ratio thereof. When the above step is taken, this effect is avoided in that in the case of the BICMOS process the substrate has a resistance which is much higher than in the case of the customary CMOS process; consequently, the substrate currents are much smaller and penetrate less far into the substrate, so that the disturbing effect is less pronounced and reaches far less. Moreover, much smaller peak currents occur in BICMOS-CML circuits upon the transition from one logic state to the complementary logic state.

The assembly formed by the detector array and the electronic read-out circuits in a further embodiment of the invention is accommodated on a common substrate of a ceramic material. In order to achieve an optimum signal-to-noise ratio for the bipolar charge amplifiers, they are adjusted for a comparatively high quiescent current. The use of the CML technique also necessitates a current which is larger than that required in the case of the customary CMOS logic. Large currents involve a high dissipation of heat. When the circuits are accommodated on a ceramic substrate, for example aluminum nitride, a suitable distribution of heat is achieved, that is, a large heat sink surface area with its inherent suitable cooling properties.

The invention will be described in detail hereinafter with reference to the Figures in which corresponding reference numerals denote corresponding elements. Therein:

FIG. 5b shows graphically the signal waveform after the filtering of the signal of FIG. 5a;

The invention will be described in detail hereinafter on the basis of an embodiment wherein the device for the analysis of materials by means of radiation is formed by an analytical X-ray apparatus, notably an X-ray diffraction apparatus. The analyzing radiation therein consists of X-rays. However, it is to be noted that the invention can be used for all other apparatus for radiation analysis in which a position-sensitive detector is used for the detection of the radiation emanating from the sample to be analyzed.

Figure 1:
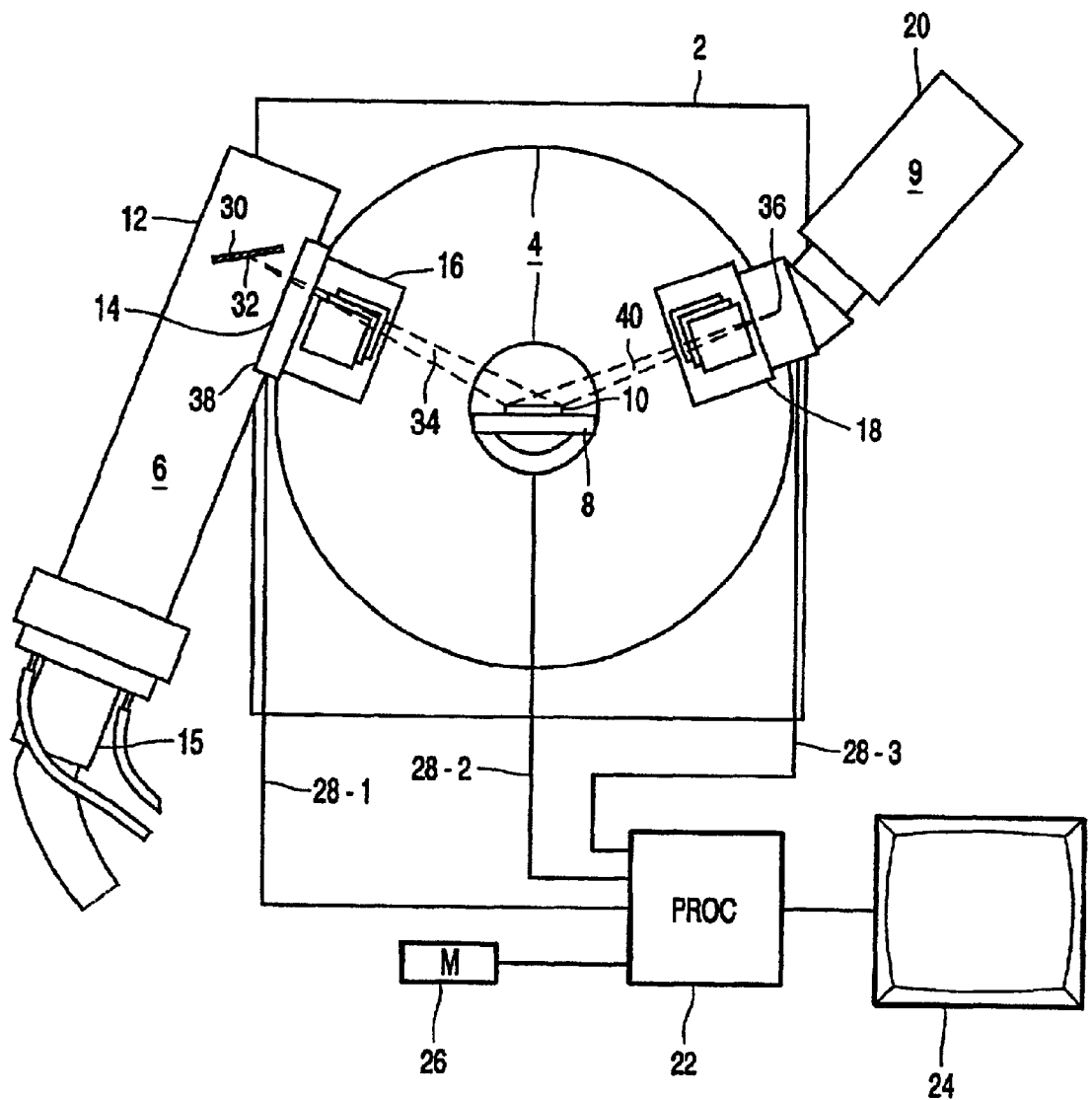
FIG. 1 is a general view of a known analytical X-ray apparatus in which the invention can be used.

FIG. 1 shows diagrammatically a known analytical X-ray apparatus, in this case being an X-ray diffraction apparatus, in which the invention can be used. A goniometer 4 therein is mounted on a frame 2. The goniometer 4 may be provided with an angle encoder for measuring the angular displacement of an X-ray source 6 and, if desired, also the angular displacement of a detection device 9. When a position sensitive detector is used, measurement of the angular displacement, however, is not necessary because the angular position of the X-rays to be measured is determined by such a detector itself. In that case an adjusting mechanism can be used instead of a goniometer for adjusting the position sensitive detector to the desired measuring range. The goniometer, moreover, is provided with a sample carrier 8 on which a sample 10 is arranged. For cases where measurement of the angular displacement of the sample is important, the sample carrier may be provided with an angle encoder. The X-ray source 6 includes a holder 12 for an X-ray tube which is not shown in this Figure and is mounted in the holder. The X-ray tube includes a high voltage connector 15 for the supply of the high voltage and the filament current for the X-ray tube. The tube holder 12 also includes an exit opening 38 for X-rays and a unit 16 for parallelizing the X-rays (a Soller slit collimator). The plates of the Soller slit collimator 16 extend parallel to the plane of drawing so that the radiation beam produced by the X-ray source 6 irradiates the sample 10 by way of a diverging beam. The detection device 9 consists of a holder 18 for a Soller slit collimator and a detector 20. The plates of the Soller slit collimator in the holder 18 also extend parallel to the plane of drawing. The X-ray source itself may be arranged so as to be stationary; in that case the sample carrier should be arranged so as to be rotatable.

The X-ray diffraction apparatus as shown in FIG. 1 also includes a processing device for processing the various measured data. This processing device consists of a central processing unit 22 (provided, if desired, with an interface device for adapting the measuring data to the processing device) which includes a memory unit 26 and a monitor 24 for the presentation of the various data and for the display of the measured and the calculated result. The X-ray source 6, mounted on the goniometer 4, the detection device 9 and the sample carrier 8 may all be provided with a unit (not shown) for determining the angular position of the respective element relative to the goniometer. A signal representing such an angular position is applied, via connection lines 28-1, 28-2 and 28-3, to the central processing unit 22.

The sample 10 is irradiated by means of X-rays from the X-ray source 6. The X-ray source includes an anode 30 (represented diagrammatically) which forms part of the X-ray tube which is not shown in this Figure. The anode 30 generates X-rays 34 which emanate via the X-ray window 38. The point wherefrom the X-rays emanate in the arrangement shown in FIG. 1 is not formed by a single point, but by a line focus 32 on the anode, which line focus extends perpendicularly to the plane of drawing. In a focusing diffractometer a focal point is formed in the point 36 of the beam that emanates from the sample, that is, at the area of junction of this beam near the entrance of the detector 20. Consequently, this arrangement has a focusing effect only in the plane of drawing and the cross-section of the beam at the area of the point of junction 36 is shaped as a line extending perpendicularly to the plane of drawing. The detector elements of a position sensitive X-ray detector are then also line-shaped and extend parallel to the focal line at the area of the point 36.

Figure 2:
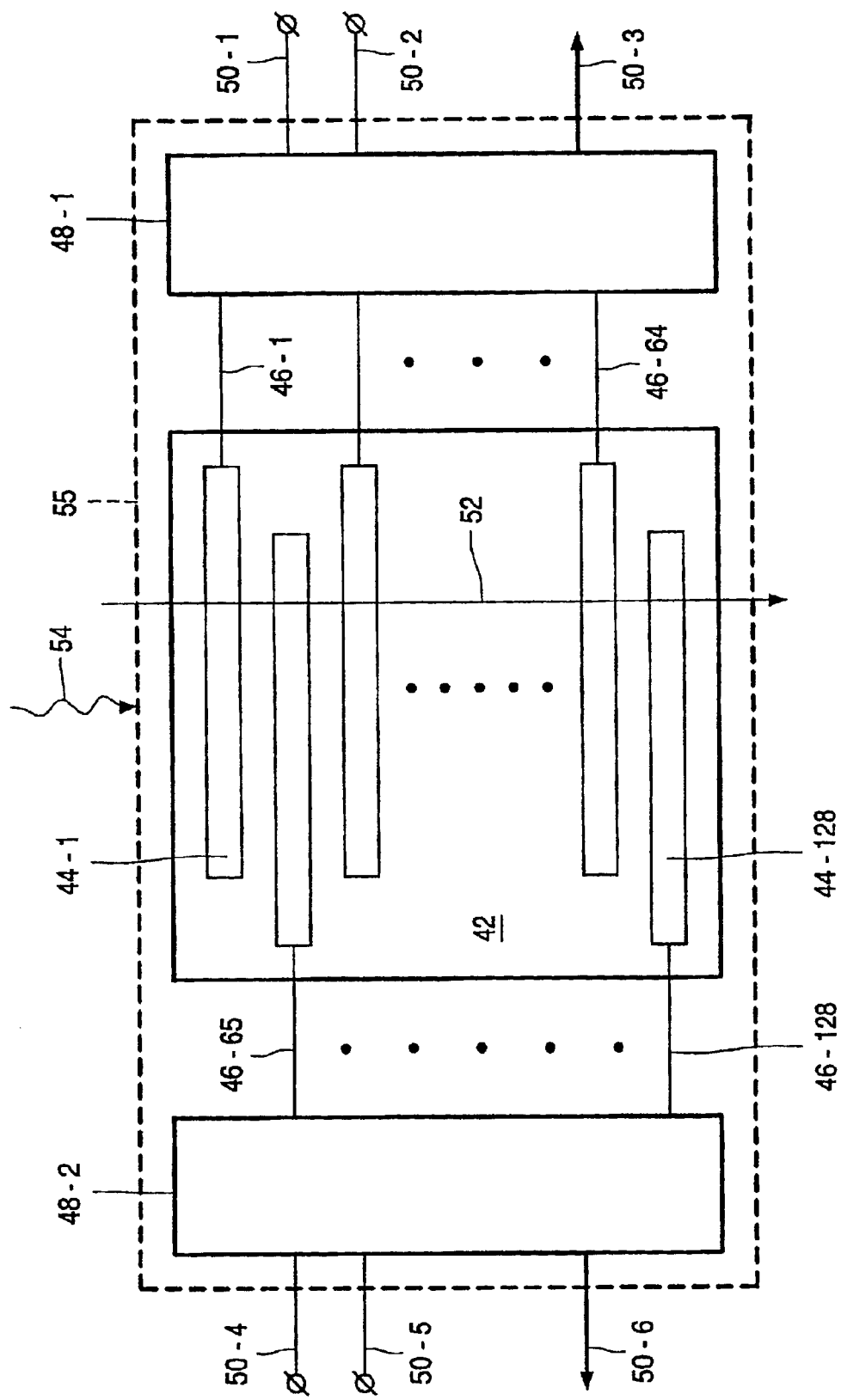
FIG. 2 is a diagrammatic view of the arrangement of the array of radiation sensitive detector elements and two groups of the electronic read-out circuit of the position sensitive detection device in accordance with the invention.

FIG. 2 illustrates diagrammatically the arrangement of the array of radiation sensitive detector elements 42 and two chips 48 which comprise 64 groups of electronic read-out circuits each, said read-out circuits comprising the charge amplifiers which are connected to the detector elements. Each of said electronic read-out circuits also includes bandpass filters and signal level comparators; an output multiplexer is also connected to the output of each of the chips in order to limit the number of output pins of the chip.

The array of radiation sensitive detector elements is denoted by the reference numeral 42 in FIG. 2. The array consists of a number of 128 detector elements 44-1 to 44-128, denoted hereinafter in general by the reference numeral 44. The construction of the array 42 will be described in detail hereinafter with reference to FIG. 4. Each of the detector elements 44-$i$ is connected, via a bond pad (not shown) on the substrate of the array 42, via a connection wire 46-$i$ and via a bond pad (not shown) on the chip 48, to its respective electronic read-out circuit in the chip 48-1 or 48-2, the input of each read-out circuit being formed by the input of a charge amplifier. After electronic processing of the signals received from each of the detector elements 44, the processed signals are applied, via a multiplexer (not shown) provided for each chip 48, to the outputs 50-1 to 50-6, that is, to the output 50 in general. Each of the outputs 50-1 and 50-4 consists of two physical conductors for the transfer of a binary signal which indicates whether an X-ray quantum has been detected or not; each of the outputs 50-2 and 50-5 consists of two physical conductors for the transfer of a binary signal which indicates whether the energy of the detected X-ray quantum is within a specified energy window or not, and each of the outputs 50-3 and 50-6 consists of a bus with twelve physical conductors for the transfer of a 6-bit digital signal which represents the address of the detector element 44-$i$ having detected the relevant X-ray quantum. The substrate of the array 42 and the substrate of the two chips 48-1 and 48-2 are provided together on a common support (55) of a ceramic material, for example of aluminum nitride. The contents of a read-out circuit on the chip 48 will be described in detail hereinafter with reference to FIG. 3.

In response to the incidence of an X-ray quantum 54, the detector element 44-$i$ struck by the quantum will output a current pulse to the associated charge amplifier. The order number i of the detector element struck is a measure of the position where the quantum is incident, so that the position sensitive direction extends perpendicularly to the longitudinal direction of the detector elements as is indicated by the direction of the arrow 52 in FIG. 2. The position resolution of the detector array is then determined by the width of the detector elements 44, that is, the dimension in the direction of the arrow 52.

Figure 3:
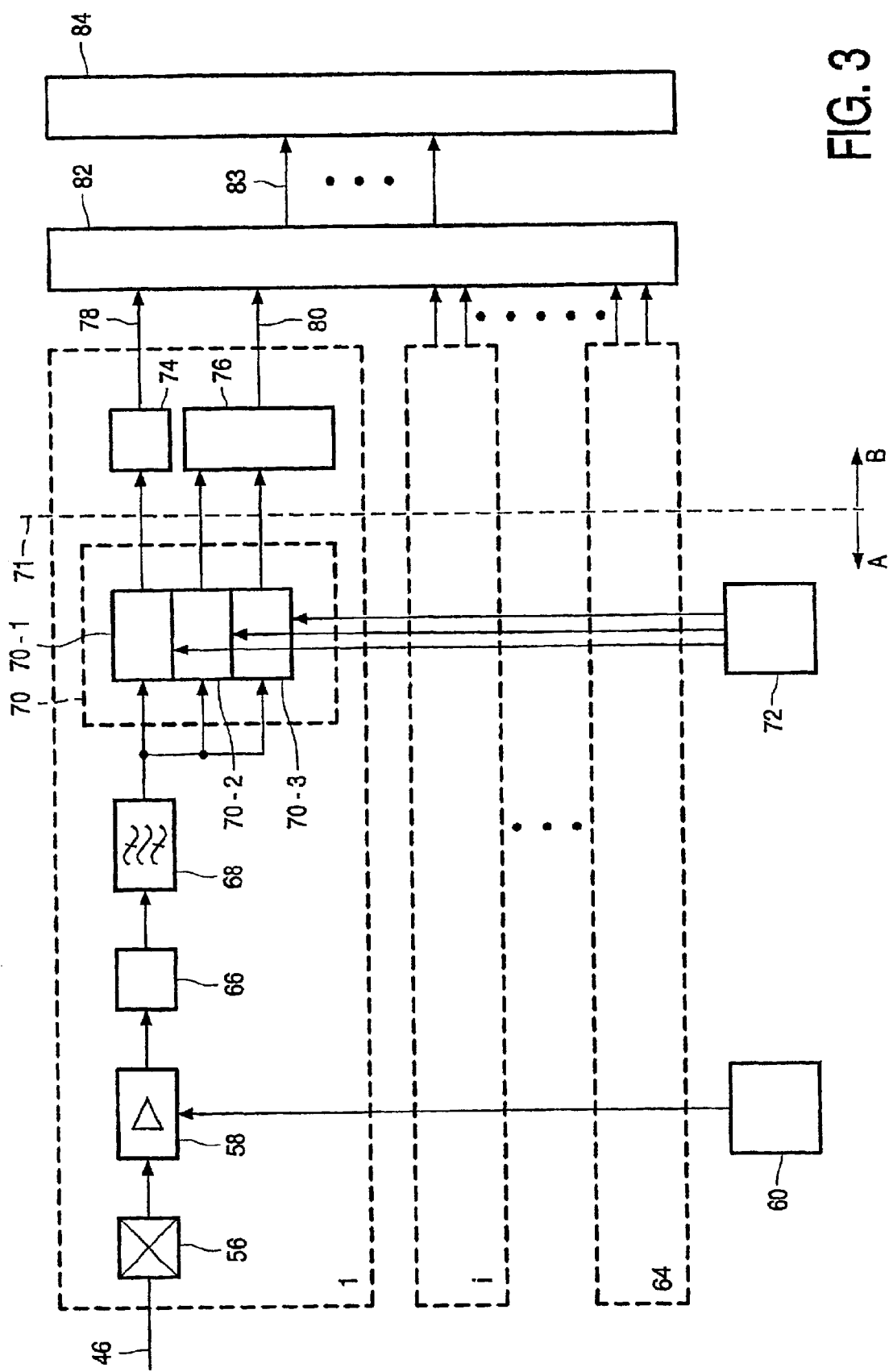
FIG. 3 is a diagrammatic view of the various functional blocks of the electronic read-out circuit shown in FIG. 2.

FIG. 3 shows diagrammatically the various functional blocks of the electronic read-out circuit in the chip 48 shown in FIG. 2. The current pulse produced by a detector element 44 is applied to the charge amplifier 58 via a bond pad (not shown in FIG. 3) on the substrate of the array 42, a connection wire 46 and a bond pad 56 on the chip 48. The charge amplifier is reset to an initial state at regular instants by means of a reset circuit 60.

A buffer circuit 66 is connected to the output of the charge amplifier 58 in order to ensure that the output of the charge amplifier 58 is not loaded by the circuits connected downstream therefrom. The signal obtained downstream from the buffer circuit 66 is filtered for further processing in a bandpass filter 68, after which the signal thus filtered is compared, in a comparator circuit 70, with preset values in order to determine whether an X-ray quantum of the intended energy (so a charge pulse of the correct value) has been received. To this end, the comparator circuit 70 consists of a noise threshold comparator 70-1 for determining whether the signal received exceeds the adjusted noise threshold, a lower level comparator 70-2 for determining whether the signal received is higher than a predetermined lowest signal level, and an upper level comparator 70-3 for determining whether the signal received is lower than a predetermined upper signal level. The comparator levels can be adjusted by means of an adjusting circuit 72. A vertical dashed line 71 in FIG. 3 denotes the separation between the sections that are constructed in an analog technique (that is, to the left of the dashed line and denoted by the letter A) and those constructed in the digital technique (that is, to the right of the dashed line and denoted by the letter D). In accordance with the invention both these sections are situated on the same substrate 55 (see FIG. 2).

A quantum detection circuit 74 is connected to the output of the noise threshold comparator 70-1, which detection circuit indicates, by way of a binary signal (the detection signal) on its output 78, whether an X-ray quantum has been detected or not. A window circuit 76 is connected to the outputs of the lower level comparator 70-2 and of the upper level comparator 70-3; this window circuit indicates whether the detected X-ray quantum is within the energy window specified by the comparators 70-2 and 70-3, that is, by way of a binary signal (the window signal) on its output 80-$i$. The bus conductor 83, connected to the output of the multiplexer 82, then transfers the binary detection signal, the binary window signal and the digital 6-bit address signal.

64 of the channels for signal processing as described above are provided for each chip 48. Thus, each channel i has a binary output 78-$i$ and a binary output 80-I; all of said outputs are connected to an output multiplexer 82 and can be applied to the central processing unit 22 (see FIG. 1), for example, via a suitable interface circuit.

All individual circuits described with reference to FIG. 3 are known to persons skilled in the relevant art and hence need not be further elucidated in respect of construction and operation.

Figure 4:
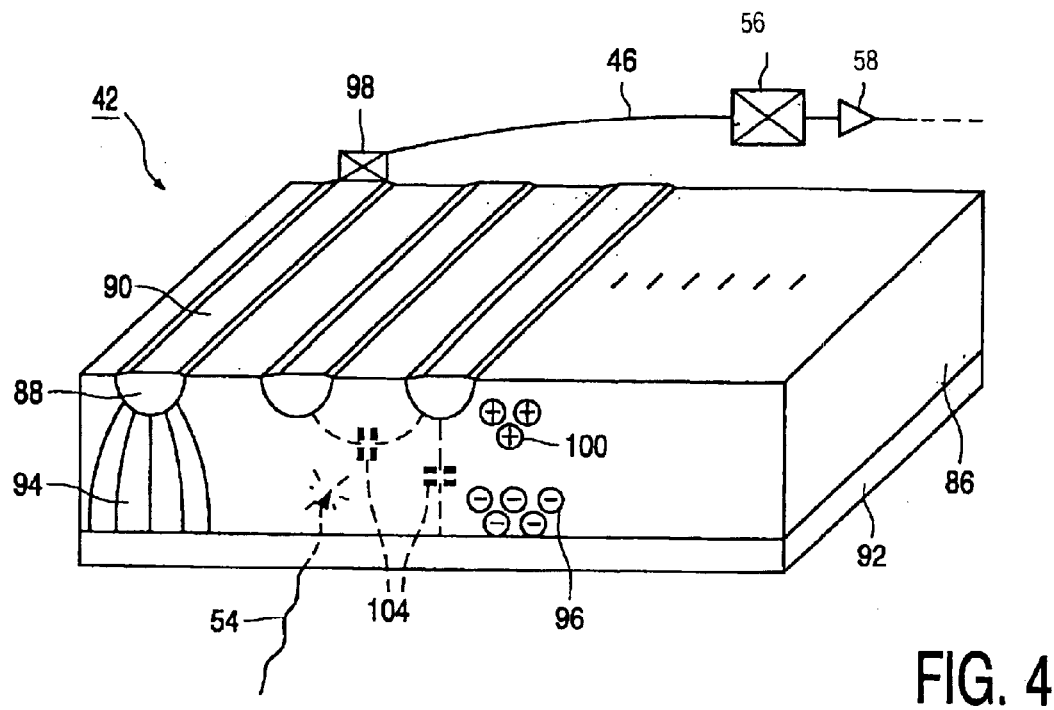
FIG. 4 is a perspective view of the construction of the array of radiation sensitive detector elements as shown in FIG. 2.

FIG. 4 is a perspective view of the construction of the array 42 of radiation sensitive detector elements as shown in FIG. 2. Said array is formed on a substrate 86 which consists of a comparatively thick layer of n-material having a high electric resistivity. Elongate recesses 88 that are filled with p-material are formed on one side of said layer. On said p-material there is provided an elongate aluminum take-off electrode 90 for signal take-off. The shape of the recess 88, and hence of the electrode 90, is such that its width is substantially smaller than its length, with the result that the shape of the electrode corresponds to the shape of an X-ray line focus to be detected. On the other side of the layer 86 there is provided a layer of $n^+$ material 92 for electrical contacting. During operation the voltage across the n+ layer 92 is, for example 80 V and that across the take-off electrode is, for example 2.5 V. The applied voltage causes an electric field whose field lines 94 are shown between the take-off electrode 90 and the n+ layer 92. This voltage difference (that is, 80–2.5 V) completely depletes the material 86, which means that there are no free charge carriers left.

During operation an X-ray quantum 54 is incident on the lower side of the layer 86. This produces a number of electron-hole pairs in said layer, said number being dependent on the energy of the X-ray quantum. When the energy of the X-ray quantum is, for example, 8 keV, the number of electron-hole pairs released is equal to the ratio of said energy to the release energy of one electron-hole pair of, for example 3.6 eV, so that approximately 2200 electron-hole pairs are released in that case. The electrons 96 of the released electron-hole pairs travel in the direction of the n+ layer 92 under the influence of the electrical field; the holes 100 move in the direction of the p-material 88, so the electrode 90. A charge pulse is thus formed in a circuit which is connected between the n+ layer 92 and the p material 88.

The shape of the recess 88, and hence of the electrode 90, is such that its width is substantially smaller than its length, so that a high position resolution can be achieved in a direction perpendicular to the longitudinal direction of the electrode 90, the greater length of this electrode nevertheless resulting in a reasonable electrode surface area, so that the detecting surface area will not become unnecessarily small and hence the detection efficiency will not be too low. Preferably, the beam of X-rays to be detected should have a line-like cross-section at the area of the detector surface. This condition is satisfied in many analytical X-ray apparatus, notably in apparatus for X-ray diffraction.

The electrode 90 terminates in a bond pad 98 which is provided on the same substrate 86. A connection line 46 extends from this bond pad 98 to a bond pad 56 which also belongs to the chip 48 (see also FIG. 3). The charge pulse taken off via the electrode 90 is thus transferred to the charge amplifier 58 of the chip 48 for further signal processing. The combination formed by the electrode 90, the p-material 88, the underlying semiconductor material 86 and the layer of n+ material 92 gives rise to a stray capacitance which is diagrammatically represented by the reference numeral 104 in the Figure; this stray capacitance 104 is observed on the output of the detector element, that is, on the input of the charge amplifier connected thereto. Because the capacitance on the input of such an amplifier determines the noise contribution by said amplifier in the amplifier chain, it is very important to design the remainder of the signal processing chain so as to be as low-noise as possible.

Figure 5A:
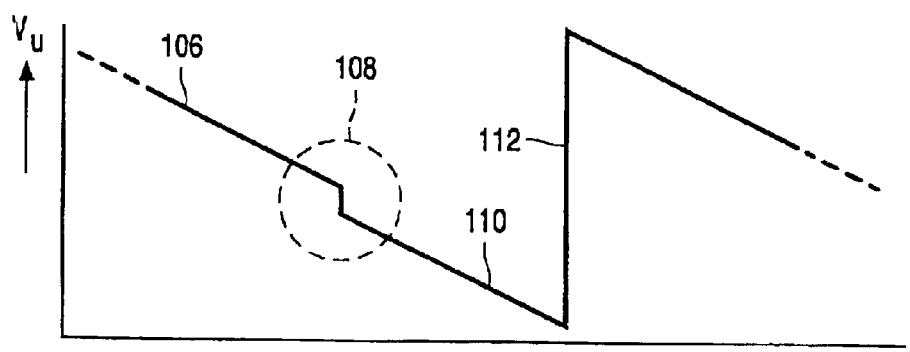
FIG. 5a illustrates graphically the signal waveform immediately behind a charge amplifier of the electronic read-out circuit.
Figure 5B:
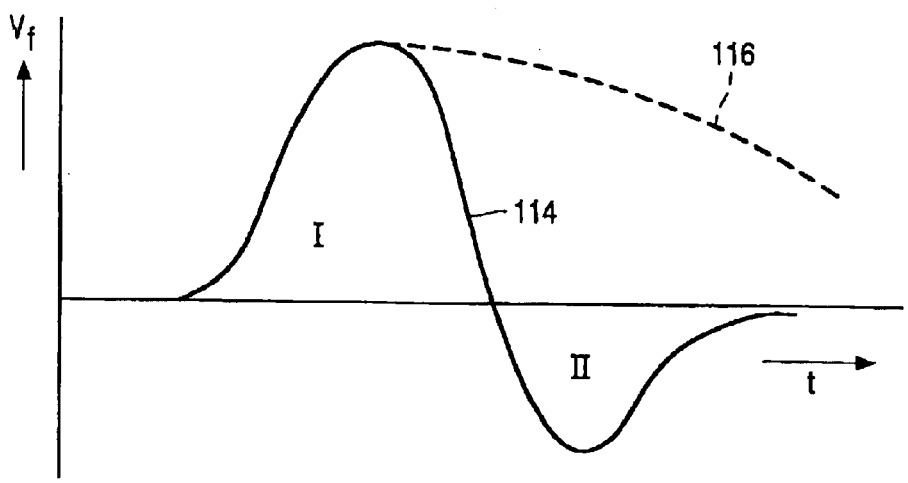

The FIGS. 5a and 5b are a graphic representation of the signal waveform immediately behind a charge amplifier of the electronic read-out circuit and after the filtering of said signal, respectively. As is generally known, a charge amplifier is provided with a capacitor which converts the charge pulse received into a voltage step which is amplified by a voltage amplifier. The inevitable leakage current through the semiconductor material of the substrate 86 charges this capacitor slowly so that the output voltage $V_u$ of the (inverting) charge amplifier varies linearly as a function of time as denoted by the linear part 106 in FIG. 5a. In the absence of a charge pulse on the input of the charge amplifier, the amplifier will be reset after some time; this means that the charge across the capacitor is set to an initial value (for example, 0 C), after which said linear variation starts again. However, when a charge pulse is presented, a transient will occur in the charge across the capacitor, so in the output voltage as denoted by the voltage transient 108 in FIG. 5a, after which the linear part continues (with a vertical shift) with the line 110 until the amplifier is reset again in conformity with the reset 112.

The signal thus obtained is digitally filtered by means of a bandpass filter whose output signal $V_f$ is represented by a solid line 114 in FIG. 5b. The surface above the time axis and below the line 114, denoted by the letter I, is then substantially equal to the surface II below the time axis and above the line 114. This effect is achieved by means of a filter which has three coincident real poles. The advantage of the above-mentioned signal waveform in conformity with the line 114 consists in that the time elapsing between the presentation of a current pulse and the detection of this pulse (that is, the electronic detection of the occurrence of a pulse) is shorter because of said signal waveform which exhibits a much faster return to the zero value than a signal waveform from, for example, a conventional bandpass filter whose waveform is denoted by the dashed line 116 in FIG. 5b for the sake of comparison. This fast return to the zero value enables a high count rate for the detector.

Figure 6A:
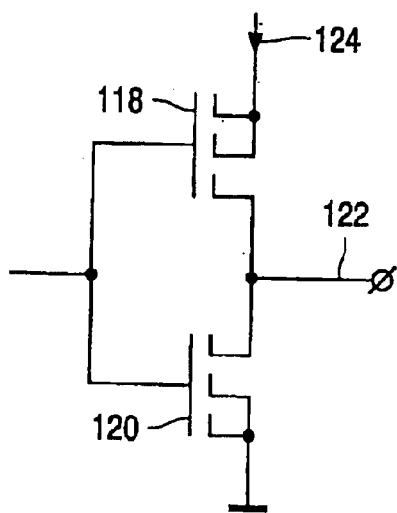
FIG. 6a shows a logic gate constructed in the CMOS technique.
Figure 6B:
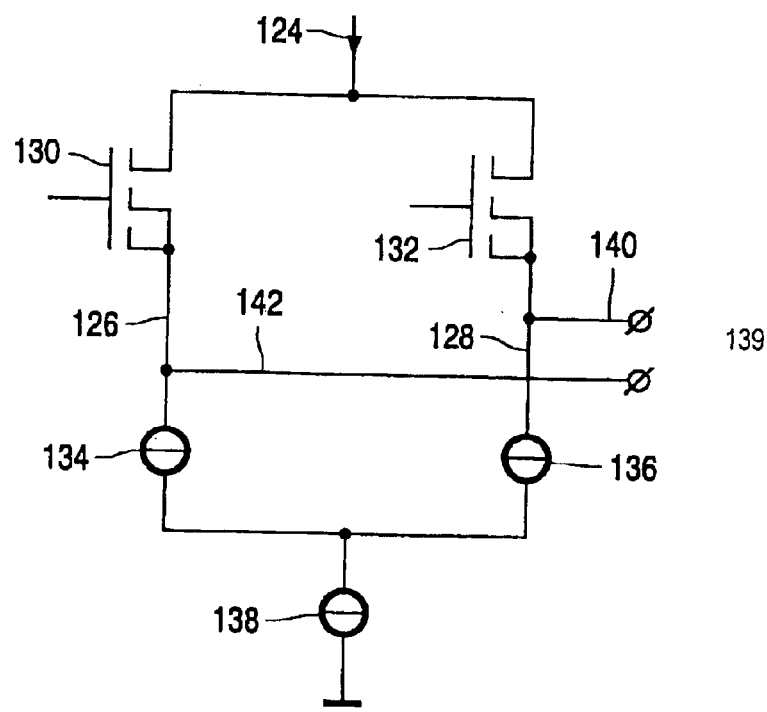
FIG. 6b shows a logic gate constructed in the CML technique.

The FIGS. 6a and 6b show a logic gate in the CMOS logic and a logic gate in the CML technique, respectively. The logic gate shown in FIG. 6a consists of two MOSFET transistors 118 and 120 which are connected in series by way of their main current path, the junction 122 constituting the output for the logic signal. In the case of a transition from a logic state to the complementary logic state there will be a reactive current to the substrate. This current is produced as follows. In a first logic state of the gate a current is conducted through the output 122 which is directed inwards; in the complementary logic state a current is conducted through the output 122 which is directed outwards. In the latter case the current flows from the supply point 124 and through the transistor 118 to the output 122, so that the transistor 120 is not conductive and hence no current flows to the substrate. In the former case the current flows from the output 122 and through the transistor 120 to the substrate, so that the transistor 120 is conductive. In that case a current does flow to the substrate. Upon transition of the logic state, therefore, a current difference occurs in the form of a pulse-shaped peak current or reactive current. Because the charge amplifiers constructed in the bipolar technique are also provided on the same substrate, this pulse-shaped peak current will contribute to the noise of the charge amplifiers; this would degrade the signal-to-noise ratio thereof.

The described problem is solved by using a logic gate which is constructed in the form of CML logic as shown in FIG. 6b. This gate consists of two parallel branches 126 and 128 which are connected in series with a current source 138. Each of the two parallel branches 126 and 128 consists of a MOSFET transistor 130, 132 and a current source 134, 136, respectively. The output of this gate is formed by the two junctions 139 and 140; the difference voltage between these two junctions represents the logic value. In the case of a transition between two logic states, the current decrease in one transistor, for example the transistor 130, equals the current increase in the other transistor 132 and vice versa. The substrate current is the sum of these two currents and does not change. Consequently, the undesirable pulse-shaped peak current will not occur so that it cannot make a noise contribution in the analog processing chain on the substrate.

What is claimed is:

1. A device for analysis of materials by means of radiation, including a radiation source (6) for producing the radiation (34), a sample location (8) for accommodating a sample (10) of the material to be analyzed, a position sensitive detection device (9) for detecting the radiation (40) emanating from the sample, which detection device includes an array (42) of radiation sensitive detector elements (44), an electronic read-out circuit (48) which is connected to the detector array and includes charge amplifiers (58) in a one-to-one relationship with the detector elements (44), the input of said charge amplifiers being connected to a respective one of the detector elements, characterized in that the charge amplifiers (58) are constructed in the integrated bipolar technique, and that the electronic read-out circuit (48) includes digital signal processing circuits (74–82) which are connected to the outputs of the charge amplifiers and are constructed in the digital technique, wherein the digital signal processing circuits are accommodated on the same substrate as the charge amplifiers 58, and wherein the digital signal processing circuits are constructed by means of a BICMOS process in the form of the Current Mode Logic (CML) technique.

2. A device as claimed in claim 1, wherein the assembly formed by the detector array (42) and the electronic read-out circuit (48) is accommodated on a common support (55) made of a ceramic material.

3. A position sensitive detection device (9) for detecting the radiation (40) emanating from the sample, which detection device includes an array (42) of radiation sensitive detector elements (44), an electronic read-out circuit (48) which is connected to the detector array and includes charge amplifiers (58) in a one-to-one relationship with the detector elements (44), the input of said charge amplifiers being connected to a respective one of the detector elements, characterized in that the charge amplifiers (58) are constructed in the integrated bipolar technique, and that the electronic read-out circuit (48) includes digital signal processing circuits (74–82) which are connected to the outputs of the charge amplifiers and are constructed in the digital technique, wherein the digital signal processing circuits are accommodated on the same substrate as the charge amplifiers 58, and wherein the digital signal processing circuits are constructed by means of a BICMOS process in the form of the Current Mode Logic (CML) technique.

* * * * *